United States Patent [19]

Bhagat et al.

[11] Patent Number: 4,668,374

[45] Date of Patent: May 26, 1987

[54] GAS SENSOR AND METHOD OF FABRICATING SAME

[75] Inventors: Jayant K. Bhagat, Troy; David S. Howarth, Rochester, both of Mich.

[73] Assignee: General Motors Corporation, Detroit, Mich.

[21] Appl. No.: 882,689

[22] Filed: Jul. 7, 1986

[51] Int. Cl.[4] .................................................. G01N 27/58
[52] U.S. Cl. ..................................... 204/412; 29/592 R; 204/425; 204/426; 357/25
[58] Field of Search ................ 204/412, 425, 1 S, 426; 29/592 R; 357/25

[56] References Cited

U.S. PATENT DOCUMENTS

| | | | |
|---|---|---|---|
| 3,844,920 | 10/1974 | Burgett | 204/428 |
| 3,907,657 | 9/1975 | Heijne | 204/406 |
| 4,244,798 | 1/1981 | Gold | 204/192.15 |
| 4,253,931 | 3/1981 | Gold | 204/192.15 |
| 4,253,934 | 3/1981 | Berg | 427/78 |
| 4,264,647 | 4/1981 | Trevorrow | 427/125 |
| 4,272,329 | 6/1981 | Hetrick et al. | 204/1 T |
| 4,272,330 | 6/1981 | Hetrick | 204/1 T |
| 4,272,331 | 6/1981 | Hetrick | 204/1 T |
| 4,303,490 | 12/1981 | Gold | 204/192.15 |
| 4,384,935 | 5/1983 | DeJong | 204/406 |
| 4,505,799 | 3/1985 | Baxter | 204/416 |

OTHER PUBLICATIONS

J. Weissbart and R. Ruka, "Oxygen Gauge", The Review of Scientific Instruments, 32 (May, 1961).

William J. Fleming et al, "Sensor for On-Vehicle Detection of Engine Exhaust Gas Composition", General Motors' Research Publication GMR-1325, Feb. 20, 1973 (This paper was prepared for presentation at the SAE National Automobile Engineering Meeting, Detroit, Mich.).

May 14-18, 1973 and Published in the Proceedings thereof as SAE 730, D. S. Eddy, "Physical Principals of the Zirconia Exhaust Gas Sensor", General Motors Research Publication GMR-1480, Nov. 14, 1973 (This paper was prepared for presentation at the IEEE Vehicular Technology Conference, Cleveland, Ohio, Dec. 4-5, 1973).

D. M. Haaland, "Internal-Reference Solid-Electrolyte Oxygen Sensor", Analytic Chemistry, 49, (Oct. 1977), pp. 1813–1817.

C. Franx, "A Dynamic Oxygen Sensor OSU-20", Proc. Sensors and Actuators Symposium, Nov. 1-2, 1984, Kluer, Deventer, Netherlands, 1985.

C. Franx, "A Dynamic Oxygen Sensor with Zero Temperature Coefficient", Sensors and Actuators, 7 (Aug., 1985), pp. 263–270.

D. M. Haaland, "Noncatalytic Electrodes for Solid-Electrolyte Oxygen Sensors", J. Electrochemical Soc., 127, (Apr., 1980), pp. 796–804.

*Primary Examiner*—G. L. Kaplan
*Attorney, Agent, or Firm*—Robert J. Wallace

[57] ABSTRACT

A rapid-response gas sensor for measuring the relative presence of a gas in a mixture of gases and its method of manufacture. The sensor is fabricated using microelectronics technology to form multiple thin-film solid-electrolyte pump and sense cells within a hermetically sealed sensor cavity.

53 Claims, 25 Drawing Figures

GAS SENSOR AND METHOD OF FABRICATING SAME

FIELD OF INVENTION

The present invention generally relates to gas sensors of the electro-chemical type. More particularly, this invention relates to what are commonly referred to as internal-reference, solid-electrolyte gas sensors and to methods of manufacturing these sensors using microelectronics processing techniques.

BACKGROUND OF THE INVENTION

Gas sensors are used in a variety of applications such as to detect noxious or explosive gases, or to measure the quantity of a particular gaseous component in a mixture of gases. For example, gas sensors are used to monitor oxygen in certain air-fired shale retorting processes and coal gasification processes. In combustion control applications, information regarding the relative concentrations of combustion gas components can be used to generate a feedback signal to regulate the combustion process. This control provides a means for maximizing efficient fuel usage and for managing exhaust emissions.

One type of known gas sensor uses a solid electrolyte material which exhibits ion-specific conduction to "sense" the quantity of a particular gas in a gas mixture. Porous metal electrodes are attached to the opposite faces of the solid electrolyte to form a galvanic cell. By exposing one face of the cell to a reference gas of known concentration and the opposite face to an unknown concentration of the same gas, the cell generates a galvanic potential which can be used to determine the unknown concentration. The galvanic potential is produced by the gas concentration gradient across the electrolyte body. If there is no concentration gradient, the cell voltage is zero. The voltage can be related to the gas partial pressure differential at the two electrolyte faces by the Nernst equation: $E = AT \ln[P_1/P_2]$ where E is the galvanic voltage, T is the absolute temperature of the gas, $P_1/P_2$ is the ratio of partial pressures of the gas, and $A = R/4F$, where R is the universal gas constant and F is the Faraday constant.

Gas sensors have been devised which comprise both a solid-electrolyte, galvanic cell and a device incorporated in the sensor which generates an internal gas reference. These gas sensors generate their own internal reference through a second solid electrolyte cell having porous metal electrodes which electrochemically "pumps" gas into and out of a fixed-volume, hermetically sealed cavity within the sensor. An external power source is used to apply a potential across the solid electrolyte body. Gas molecules are ionized at the interface of the gas, the negative electrode and the electrolyte by acquiring electrons flowing through the negative electrode. These ions then move through the solid electrolyte body by ionic conduction. At the positive electrode, gas ions give up electrons and recombine into gas molecules. By reversing the polarity of the circuit, gas can be transported in either direction. By pumping gas into and out of the sealed cavity through the solid electrolyte, while simultaneously sensing the partial pressure differential between the cavity gas and the external gas with a solid electrolyte galvanic cell, these internal-reference, solid-electrolyte gas sensors measure the concentration of a particular gas in a gas mixture environment.

One particular application for gas sensors of the type described above is in the automotive industry for use in analyzing automobile exhaust gases. It is known that the partial pressure of oxygen in automobile exhaust gas has a direct relationship to engine air-to-fuel ratio. By measuring the oxygen content of the exhaust gas, a feedback signal can be generated which allows the air-to-fuel ratio to be altered in order to achieve optimum combustion conditions. This control over engine combustion facilitates economical fuel usage and provides a means for regulating exhaust emissions. In order for a gas sensor to generate a signal which can be used in an automotive feedback system, the sensor must be accurate and capable of completing its analysis very rapidly. For example, an automotive exhaust gas sensor should have a response time of less than 0.1 second at a minimum temperature of 300° C. and a minimum oxygen concentration of about eight percent. The sensor must be airtight to prevent the leakage of oxygen into or out of the sealed chamber and be free of any source of current leakage which can be caused by electronic conduction in the electrolyte body. Both types of leakage would produce false sensor readings. The sensor must also have sufficient structural integrity to absorb shock associated with use in an automobile as well as have the ability to withstand thermal expansion of its materials over a temperature range of at least −40° C. to 800° C. Finally, such a sensor must be suited to be mass-produced.

Internal-reference, solid-electrolyte gas sensors have in the past been constructed from discrete components. A typical sensor having this construction is disclosed in U.S. Pat. No. 3,907,657 to Heijne et al. Two solid-electrolyte discs are coated on their opposite faces with porous metal electrodes and then bonded to opposite ends of a ceramic or metal, e.g. platinum, cylinder to form a sealed cavity. The cavity serves as the reference chamber into and out of which a selected gas is pumped through one electrolyte disc by a reversible constant current. In the ceramic cylinder-type of sensor, a passage through the cylinder wall must be made in order to connect leads to the inner electrodes. These lead pathways must then be hermetically sealed. In the platinum type of sensor, the platinum cylinder body provides a path for electrical contact with the inner electrodes. Leads are attached respectively to the internal and external electrodes by spot welding. Gas sensors fabricated from discrete components in the manner described above are extremely fragile and are difficult to accurately replicate.

Since sensor response time is proportional to the cavity volume, attempts have been made to reduce the size of conventional discrete gas sensors. However, conventional sensor designs and fabrication techniques prevent significant sensor miniaturization due to inherent limitations in the materials used and assembly difficulties. Prior attempts in producing a miniaturized gas sensor have resulted in a discrete component assembly having an internal volume of approximately 0.16 mm$^3$ with pump electrolyte cell wall thicknesses of approximately 0.75 mm. The response time of such a sensor is at best approximately 0.5 second in a mixture of gases containing about ten percent oxygen. This response time is much too slow for any meaningful automotive exhaust feedback application.

The rate of gas transport through the pump cell can be increased or decreased by increasing or decreasing the cell voltage. However, the amount of gas which can pass through the cell at a given temperature and voltage is limited by the resistance of the electrolyte to ionic conduction. Also, an increase in electrolyte cell thickness is accompanied by a proportional increase in its resistance to ion conduction. Although thinning the cell increases the ionic conductivity, it decreases the structural integrity of the electrolyte which must at least be sufficient to withstand slight pressure differentials across its body. It is also important to observe that when the voltage applied to the pump cell is increased above a certain threshold value, the electrolyte undergoes electrochemical reduction which can lead to failure of the material. Therefore, the pump voltage must not exceed the reduction potential of the specific electrolyte material used in the sensor.

SUMMARY OF THE INVENTION

In accordance with the present invention, we have discovered that a practical gas sensor for automotive applications can be fabricated using planar techniques adapted from microelectronics fabrication technology. The present invention provides a novel internal-reference, solid-electrolyte gas sensor fabricated by thin-film deposition and patterning techniques. The sensor comprises a first silicon dioxide-coated, electrically conductive planar substrate having a plurality of solid-electrolyte cells which are deposited and patterned on the substrate using conventional thin-film processing techniques. The electrolyte cells are anchored to the planar substrate by an overlying silicon dioxide layer and preferably by an additional layer of silicon nitride. Contact windows are etched through these anchoring layers to provide access for a porous metal electrode which is deposited through the windows and in contact with one face of the electrolyte cells and the first substrate.

A second planar substrate having a precisely etched cavity is bonded to said first substrate to form a hermetically-sealed chamber which houses the electrolyte cells therewithin. External contact windows are anisotropically etched through the bottom surface of said first substrate to reach the opposite or exterior face of the electrolyte cells. Two external porous metal electrodes are deposited in these external contact windows. The external electrodes are electrically separated from the sensor body by an insulative oxide layer. A third, common external metal electrode is formed by vapor deposition and patterning techniques on the exterior side of the first substrate and is thus electrically connected with the internal electrode through the conductive substrate.

In an alternate embodiment, a modified metallization scheme is used to form the interior electrodes using a three-layer structure which improves the adhesion of the electrodes to the silicon body and which reduces oxidation of the electrode-to-silicon bond.

In another embodiment, the electrolyte cells are formed on an oxide-coated layer of polysilicon which is isotropically etched to create external electrode contact windows.

In a further embodiment, a plurality of the electrolyte cells are formed in an array on a substrate.

It is thus a primary object of the present invention to provide a solid-electrolyte, internal-reference gas sensor which has a rapid response time and which can be mass-produced using conventional thin-film processing techniques.

It is also an object of this invention to provide a method of fabricating an internal-reference gas sensor having a hermetically sealed chamber with a preselected internal volume.

A further object of this invention is to provide a solid electrolyte, internal-reference gas sensor which is formed from semiconductor wafers.

Still another object of the present invention is to provide an internal-reference sensor which utilizes a semiconductor sensor body as a conductive path between the interior electrode and an exterior electrode.

Still another object of the present invention is to provide a solid-electrolyte, internal-reference gas sensor formed from a silicon body which has a strong silicon-to-silicon bond which is resistant to oxidation.

A further object of the present invention to provide a method of forming precise contact windows in a gas sensor body by forming electrolyte cells on an oxide-coated polysilicon substrate.

These and other objects of the invention will be made clear or will become apparent during the course of the following description of a preferred embodiment of the invention.

DETAILED DESCRIPTION OF THE INVENTION

Figure 1:
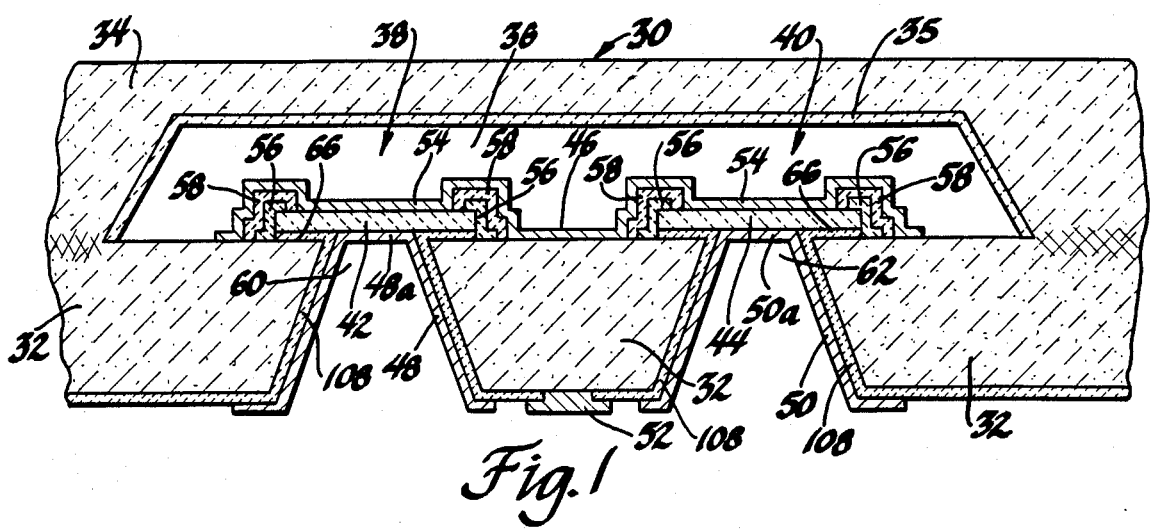
FIG. 1 is a fragmentary cross-sectional view of a gas sensor in accordance with the present invention and illustrates the pump and sense cells and the external and internal electrodes.

Referring first to FIG. 1, the present invention relates to a gas sensor generally indicated by 30 for sensing the relative concentration of a selected gas within a gaseous environment, such as the exhaust from an internal combustion engine. In an exhaust gas sensing application, the sensor 30 is employed to sense the relative concentration of oxygen in the exhaust gas and produces a feedback signal indicative of the oxygen concentration, which can be used to adjust the air/fuel ratio of the engine. As will be discussed later below, the gas sensor 30 is well adapted to operate at temperatures as low as 300° C. and provides a response time of approximately 0.1 seconds, i.e. the sensor 30 provides an output signal indicating the gas concentration within 0.1 seconds of a change in such concentration. This rapid response time is due, in part, to the fact that the sensor 30 is fabricated using microelectronics technology and is therefore quite small, typically having an internal cavity occupying a volume between 2 and 20 nanoliters.

The sensor 30 depicted in FIG. 1 broadly comprises a bottom, planar substrate 32, an upper substrate defining a top cover 34, a pump cell 38 and a sense cell 40. Although only a single pump cell and sense cell 38, 40 respectively are depicted in the sensor 30 of FIG. 1, it is to be expressly understood that the sensor 30 may include more than one pump cell 38 or sense cell 40. In fact, as will be discussed below, the sensor 30 may include an array of pump cells 38 and sense cells 40 formed on the substrate 32.

The cover 34, which can also be considered as a substrate, may consist of any suitable material which can be bonded to the lower substrate to form a hermetic seal. For high temperature applications, i.e. at temperatures greater than 500° C., the cover 34 preferably comprises a semiconductor material such as silicon in which there is formed in interior cavity 36 which defines a fixed volume or reference chamber into and from which the selected gas may be pumped. The interior of the silicon top cover 34 which defines the cavity 36 is preferably coated with an oxidation-resistant material 35 such as silicon nitride. Layer 35 can also be a multiplicity of oxidation-resistant layers, such as shown in FIGS. 12-22. The oxidation-resistant coating 35 prevents oxidation of the interior of the cover 34, thus preventing the volume of the cavity 36 from changing.

The substrate 32 is preferably formed of a conductive or semiconductive material, such as silicon and has a pair of spaced apart windows 60, 62 respectively formed therethrough which respectively register with the pump and sense cells 38, 40. The pump and sense cells 38 and 40 are disposed on silicon dioxide islands 66 on the top surface of the substrate 32, within the cavity 36. A layer or film 42 of a suitable electrolyte overlies the window 60 on the substrate 32. The particular electrolyte material chosen as the layer 42 is dependent upon the particular gas to be sensed. In the case of an oxygen sensor, the electrolyte layer 42 may comprise yttria ($Y_2O_3$) stabilized zirconia ($ZrO_2$) because of its relatively high conductivity of oxygen ions. The use of $Y_2O_3$ (approximately 8 to 10 mole percent) in the $ZrO_2$ achieves a mainly cubic phase which has the highest ionic conductivity needed for efficient galvanic reaction. Additionally, the use of $Y_2O_3$ as a stabilizer eliminates the volume expansion of pure $ZrO_2$ which is caused by the tetragonal to monoclinic phase transition which would otherwise result in catastrophic failure of the $ZrO_2$. The specific amount of $Y_2O_3$ employed as a stabilizer will vary depending upon the particular mechanical, thermal and electrical properties which are required for the particular application. The electrolyte layer 42 must be free of pin holes and cracks, since such defects impair its mechanical stability and may result in short circuiting of ion conduction by electronic conduction, thereby causing a reduction in the Nernst emf.

The electrolyte layer 42 is "anchored" to the silicon substrate 32 by means of a layer of oxidized polysilicon which overlies a portion of the silicon substrate 32 as well as the upper peripheral edges of the electrolyte layer 42. The $SiO_2$-Si bond between the oxidized polysilicon layer 56 and the substrate 42 is very strong and provides a means of rigidly attaching the electrolyte layer 42 to the substrate 32. The electrolyte layer 42, which is approximately 1 micron thick, has a larger thermal expansion coefficient than that of the silicon substrate 32. In those applications in which a substantial fluctuation exits in the ambient environment, such as with a stream of exhaust gas where temperatures can fluctuate widely, relatively large thermal stresses are applied to the electrolyte layer 42 which can cause it to fail. The oxidized polysilicon layer 56 is thus intended to prevent stress failure of the electrolyte layer 42.

It should be noted that the electrolyte layer 42 is somewhat flexible and flexes in response to the pressure differential on its opposite sides due to a pressure differential of the gas within the cavity 36 and that of the ambient, surrounding environment. Since force is proportional to the area of the electrolyte layer 42 which is exposed to the gases, it is desirable to minimize this exposed area to in turn reduce the amount of flexing. As will be discussed below, it is possible to electrically interconnect a number of either the pump cells 38 or sense cells 40 while maintaining them structurally disconnected. Such an approach can provide the necessary surface area of electrolyte layer 42 to provide the required sensitivity while obviating structural problems caused by severe flexing of the film 42.

The combination of the electrolyte film 42 and oxidized polysilicon anchor 56 is surrounded by a layer 58 of material through which the selected gas may not diffuse. In the case of oxygen as the selected gas, the layer 58 may comprise silicon nitride ($Si_3N_4$) approximately 0.1 microns thick. The barrier layer 58 extends over the top of the anchoring layer 56 and defines a window on the upper surface of the electrolyte film 42.

The construction of the sense cell 40 is identical to that of the pump cell 38. An electrolytic film 44 of yttria stabilized $ZrO_2$ is disposed over the window 62 and is anchored in place on the silicon substrate 32 by means of an anchoring layer 56 of oxidized polysilicon. A barrier layer 58 surrounds the anchoring layer 56 and thus prevents diffusion of the selected gas through the sidewalls of the electrolytic film 44.

A common electrode 54 of a conductive metal, such as platinum, electrically connects the top face of the electrolytic films 42 and 44 with the upper surface of the silicon substrate 32 at an area indicated by the numeral 46, between the pump and sense cells 38 and 40 respectively. The interior common electrode 54 is electrically connected via the conductive silicon substrate 32 to an outer common electrode 52 formed on the bottom surface of the substrate 32. An outer pump electrode 48 includes a portion 48a which extends across the window 60 and makes ohmic contact with the lower face of the electrolytic film 42. Similarly, an outer sense electrode 50 includes a portion 50a which extends across the window 62 and makes ohmic contact with the bottom face of the electrolytic film 44. Although electrodes 48 and 50 make electrical contact with the corresponding electrolytic films 42, 44, such electrodes are electrically insulated from the semiconductor substrate 32 by means of an insulative layer 108 which may comprise, for example, silicon dioxide. The outer electrodes 48 and 50 are formed of a porous platinum having a thickness between 500 angstroms and 5000 angstroms. The porosity enhances the surface areas of the electrode portions 48a, 50a and allows greater adsorption of oxygen. Platinum as the common electrode 54 and outer electrode 48, 50 is chosen because of its excellent catalytic properties and stability under both oxidizing and reducing conditions. The pump and sense electrodes 48, 50 and the outer common electrode 52 are intended to be connected with conventional external circuitry which processes the resulting signal indicative of the amount of concentration of the selected gas.

In use, sensor 30 is introduced into a gaseous environment, such as in the stream of exhaust gas of an internal combustion engine, and is connected to appropriate external circuitry (not shown) which would normally include a pump circuit connected with the pump cell 38 and a sense circuit connected with the sense cell 40. The sense circuit would typically include an electrometer and a comparator and the pump circuit would typically include a current integrator, a regulated DC power source, an ammeter and a suitable timer. It is important to note here that it is possible to integrate the aforementioned external circuitry on the substrate 32 if desired to provide an integrated micropackage. A thermocouple can be used to determine sensor temperature during operation. The electrolyte material used to form pump cell electrolyte 42 and sense sell electrolyte 44 must, of course, exhibit selective ionic conduction toward the gas to be analyzed and negligible electronic conduction. Depending on the conductivity characteristics of the sensor materials, sensor 30 may have to attain a minimum operating temperature before it becomes operational. Once introduced in the exhaust gas stream, a positive potential is applied to external pump electrode 48. Molecules of the selected gas in chamber 36 combine with electrons supplied by the integrated constant current at the three-phase interface of gas, internal common electrode 46, and pump cell electrolyte 42 to form ions which then move by ionic transport through pump cell electrolyte 42 to its interface with external pump electrode 48. Gas ions then lose electrons to external pump electrode 48 and recombine into gas molecules. The pumping process continues until virtually all of the selected gas has been removed from the chamber, that is, until the ratio of the partial pressures of the selected gas inside chamber 36 to that in the external gaseous environment is in the range of about 0.01. As chamber 36 is evacuated of the gas, a gas concentration gradient is produced across sense cell electrolyte 44 which in turn generates a galvanic potential that is measured by the sense cell circuitry. The sense cell voltage is related to the partial pressure differential by the Nernst equation, which, in the case of oxygen, is:

$$E = AT \ln [P(O_2)_1 / P(O_2)_2]$$

where E is the galvanic voltage, T is the absolute temperature, $P(O_2)_1/P(O_2)_2$ is the ratio of the partial pressures of oxygen across sense cell electrolyte 44, and $A = R/4F$, where R is the universal gas constant and F is the Faraday constant. By detecting the rapid rise in sense cell voltage caused by the increase in the partial pressure differential of the selected gas across sense cell electrolyte 44, or, alternatively, by detecting that a threshold voltage has been reached, the sense cell circuitry determines that chamber 36 is empty and reverses the pump current. Thus, polarity reversal causes oxygen to move from the external exhaust gas through pump cell electrolyte 42 into chamber 36. The ionic transport mechanism is the same as that for the movement of gas from inside chamber 36 to the external environment. Gas is pumped from the exhaust gas into chamber 36 until the partial pressure of gas in chamber 36 is equal to that in the external gas environment. In other words, the chamber is filled to the point where the ratio of the partial pressure of the selected gas inside the chamber to the partial pressure of the selected gas outside the chamber is 1. Again, the sense cell circuitry, detecting zero voltage output at sense cell electrolyte 38, reverses the current polarity at pump cell electrolyte 42. This completes one cycle of operation of the sensor 30. Sensor 30 is continuously cycled between the two end points, i.e. "chamber full" and "chamber empty". The amount of current required to fill or empty the chamber is related to the number of moles of gas actually pumped. Since gas is pumped into or out of chamber 36 at a linear rate by the constant current, the amount of time required to make the transition between endpoints is related to the concentration of the subject gas in the exhaust. Specifically, in the case of an oxygen sensor, the fundamental equation which describes the sensor operation is:

$$T = P(O_2)_{exh} \cdot (V/IT) \cdot C \cdot [e^{-Ef/AT} - e^{-Ei/AT}]$$

where T is the period of oscillation, P is the partial pressure of oxygen in the exhaust, I is the absolute of the current pump, T is the absolute temperature of the cell, V is the volume of chamber, and C is a collection of fixed geometry terms and fundamental constants, such as the number of electrons required to transport 1 oxygen ion. The concentration of the subject gas component in the exhaust gas can thus be determined.

Figure 2:
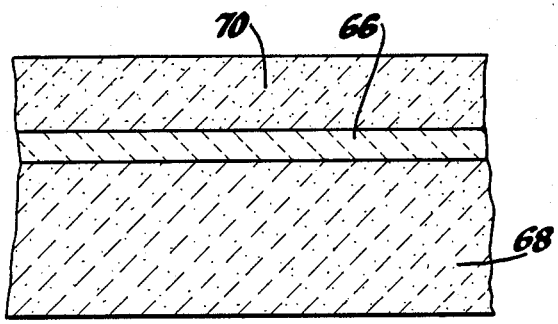
FIG. 2 is a cross-sectional view illustrating an oxidized silicon substrate on which a layer of solid electrolyte has been deposited in a preliminary step of a process for forming the electrolyte cells of the sensor shown in FIG. 1.

Having described the gas sensor 30 and its use, a novel method for constructing a gas sensor such as gas sensor 30 will now be described. Referring to FIG. 2, only one of the cells is shown because they are made in the same way. Hence, the view can be enlarged for better clarity. A layer 66 of silicon dioxide is first deposited on a (100) oriented silicon wafer 68 which defines the substrate 32 of the finished gas sensor shown in FIG. 1. The silicon dioxide layer 66 can be of any convenient thickness but is preferably from about 0.1 to 0.2 microns thick. Since the silicon wafer 68 will serve as the electrical lead to the internal common electrode (52 in FIG. 1), it should have a resistivity in the range of about 0.5 to 5 ohm-centimeters. Any conventional p or n-doped silicon wafer would be suitable. Where the sensor 30 is used at operating temperatures exceeding approximately 300° C., an undoped silicon wafer will have sufficient conductivity. The silicon wafer 68 may vary somewhat in thickness, but a thickness of about 2 or 3 millimeters is preferred to construct a device having the desired characteristics. The silicion dioxide layer 66 serves as an insulative base for the electrolyte cells 42, 44 to prevent any unwanted ionic or electric conduction between the silicon cell wafer 68 (substrate 32 in FIG. 1) and the electrolyte cells 42, 44. Alternatively, layer 66 can be formed on the silicon cell wafer 68 by oxidizing wafer 68. A layer of silicon nitride about 0.1 micron thick (not shown) is deposited on the silicon dioxide layer 66. Depending upon the thermal expansion coefficient of the electrolyte material, a layer of aluminum oxide or a layer of silicon dioxide followed by an aluminum oxide overlay may be preferred in lieu of the silicon dioxide or silicon dioxide-silicon nitride layers.

The next step in the manufacturing process involves depositing electrolyte material as a blanket layer 70 over the upper layer 66 of silicon dioxide. The blanket electrolyte layer 70 can be deposited using any conventional deposition technique which is compatible with the particular electrolyte material employed. In the case of an oxygen sensor, we prefer to use a stabilized zirconia electrolyte although somewhat more exotic materials, which are well known in the art, have sufficient oxygen ion conductivity at automotive exhaust operating temperatures to be used successfully in the practice of the present invention. For example, thorium dioxide may be a suitable electrolyte material for use in the construction of an oxygen sensor using the fabrication process of the present invention. The electronic conduction of the material must obviously be negligible at operating conditions.

In order for the zirconia to have the requisite oxygen ion conductivity needed for successful sensor operation, it must be primarily in the cubic phase in the solid state. It is known that the addition of a rare earth oxide to the zirconia will achieve this phase transition and we have found, in particular, that the addition of from about 4 to 10 mole percent yttria, and preferably from about 6 to 8 mole percent yttria, to the zirconia results in good ionic conductivity while maintaining adequate thermal and mechanical properties. That is, the electrolyte film must be sufficiently strong to withstand the pressure differentials which are encountered and, in an automotive context, have sufficient strength to withstand shocks which may be encountered. This degree of stabilization with yttria also reduces the thermal expansion of the zirconia which otherwise may cause the zirconia film to break loose from the substrate during temperature fluctuations. While the addition of greater amounts of rare earth oxides improves ionic conductivity, there is a concomitant loss of thermal and mechanical stability. Of course, increased electrolyte conductivity allows thinner electrolyte films to be used. Calcium oxide may be used as the stabilizing agent, however, it is subject to attack by water vapor which may lead to fracture of the electrolyte. Ytterbium oxide and scandium oxide are also suitable, although they are currently somewhat more expensive than yttrium oxide.

The electrolyte material is deposited to form a blanket layer 70 having a thickness of from about 0.2 to 1.5 microns. Deposition may be by chemical vapor deposition, RF sputtering or metal organic deposition as well as by other deposition techniques. We prefer to use RF sputtering. The electrolyte film must not contain any pinholes or cracks which would interfere with ionic conduction and lessen the film's mechanical integrity. The electrolyte film can be annealed immediately after it has been deposited on the substrate or this step can be delayed until subsequent processing.

Figure 3:
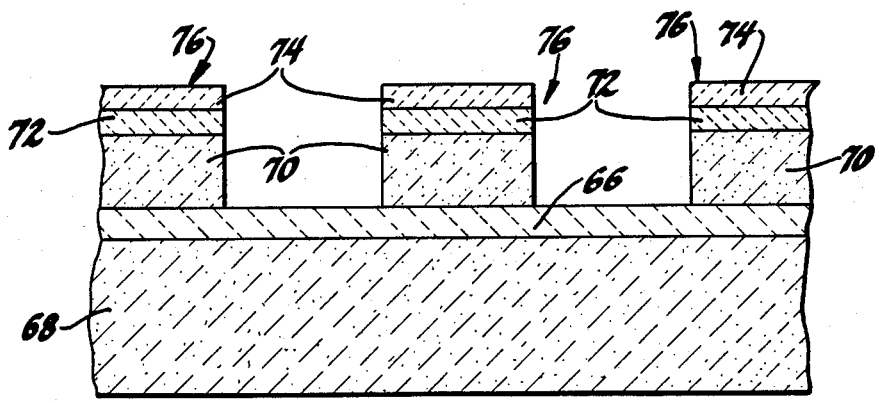
FIG. 3 is a cross sectional view illustrating the next step in forming the electrolyte cells in which the geometry of the cells is patterned.

Referring now to FIG. 3, using standard lithography and etching techniques, the electrolyte layer 70 is patterned to form freestanding electrolyte cells 76. The precise geometry of electrolyte cells 76 may vary according to the layout of the cell wafer. However, there obviously must be at least one sense cell and one pump cell inside each sensor cavity. In one preferred construction, the pump electrolyte is divided into two rectangles approximately 750 microns by 3460 microns. One sense electrolyte, 500 microns by 3460 microns, is placed between the two pump electrolytes. In order to achieve the requisite sensor response time, the cavity volume as stated should be between 1 and 20 nanoliters which therefore limits the size of electrolyte cells 76. The cell size is also restricted by the permissible thickness of the electrolyte film. A thicker cell requires greater pump current and/or more time for oxygen to be transported through the cell. Since the electrolyte film will flex somewhat when exposed to pressure differences which it will encounter during operation and, taking into consideration that the force exerted on the film is proportional to the area of the film exposed to the gas, it is preferred that the exposed area should be kept small. This can be accomplished by connecting a multiplicity of small electrolyte cells, for example, 110 microns square, in an array such as that shown in FIG. 25, wherein the exposed areas of each of the cells is relatively small. That is, the cells can be electrically connected while still keeping them structurally disconnected. This method provides the equivalent surface area of a larger cell configuration and reduces the structural problems associated with larger cell surface area.

If electrolyte cells 76 are formed by plasma etching, good patterning results can be obtained using a tri-level resist scheme. This prevents excessive erosion of the photoresist which may occur when a wafer is kept in an etch bath for a long period of time. For example, $H_3PO_4$ may be used to etch the electrolyte cells by employing a suitable etch mask such as polysilicon. Polysilicon is a good mask in $H_3PO_4$ etchants since $H_3PO_4$ does not react substantially with polysilicon. As illustrated in FIG. 3, when using an $H_3PO_4$ etchant, a thin layer of polysilicon 72 is deposited on the surface of electrolyte layer 70. Polysilicon layer 72 is approximately 0.2 to 0.5 microns thick. A thin layer 74 of silicon dioxide, about 0.1 micron thick, is then grown using standard techniques over polysilicon layer 72. Photoresist adheres better to silicon dioxide than to polysilicon for wet chemical etching. Photoresist (not shown) is then patterned using conventional techniques and the resist pattern is transferred to silicon dioxide layer 74. Polysilicon layer 72 is then etched to the required cell geometry, either after the resist has been removed or without removing the resist when a fluorine plasma etch is utilized. If electrolyte layer 72 is etched using $H_3PO_4$, it is preferred that the etchant bath be maintained at a temperature of around 170° C. to about 180° C. With yttria-stabilized zirconia, etching at this temperature yields an etch rate of about 10 nanometers per minute. After electrolyte cells 76 have been etched, silicon dioxide layer 74 and polysilicon layer 72 can be removed using standard chemical or dry etching processes. Those portions of silicon dioxide layer 66 not supporting electrolyte cells 76 are also removed at this time to provide exposure of upper surface portions of substrate 68.

Figure 4:
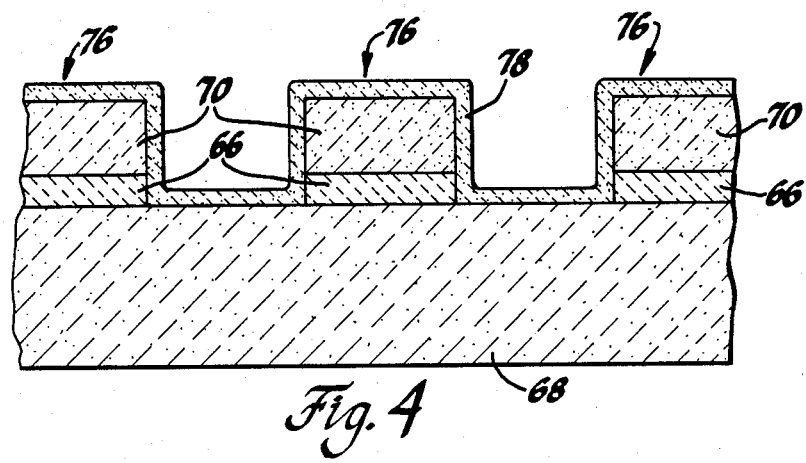
FIG. 4 is a cross-sectional view depicting the next step in forming the electrolyte cells in which a sacrificial layer of polysilicon is removed and a new layer of polysilicon is deposited to form an anchoring surface.

In order to produce a reliable sensor, the sensor must have good longevity, which is a factor determined by its structural soundness. In most instances, the electrolyte material will have a coefficient of thermal expansion greater than that of its supporting substrate. This thermal mismatch of the materials can produce stresses leading to fracture of the electrolyte film. Therefore, it is critical that the electrolyte cells be securely attached to their supporting substrate. As shown in FIG. 4, this can be achieved by depositing a layer of polysilicon 78 over the structure which, when pattern, will serve to anchor electrolyte cells 76. Polysilicon anchor layer 78 should be from about 0.1 to about 0.5 microns thick. Polysilicon layer 78 is then completely oxidized to form silicon dioxide which forms a strong bond to the silicon substrate 68.

Figure 5:
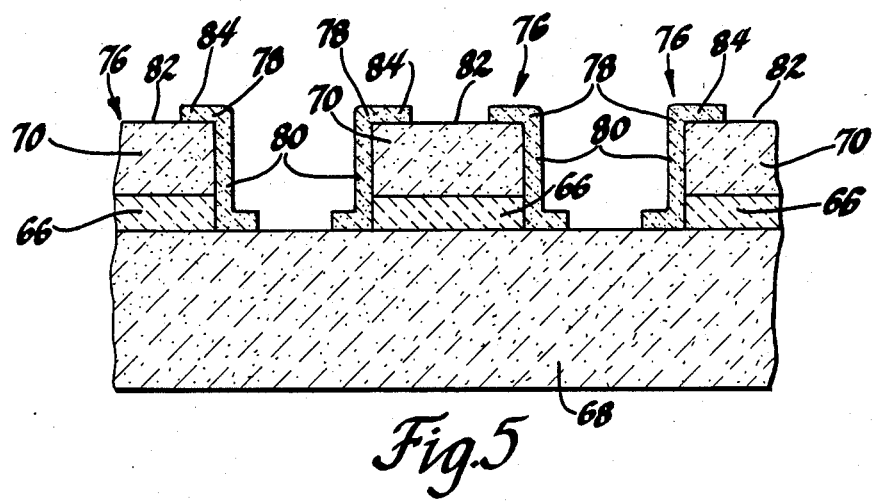
FIG. 5 is a cross-sectional view showing the next step in forming the electrolyte cells in which the polysilicon layer is oxidized and patterned to form silicon dioxide cell anchors and contact windows.

Referring to FIG. 5, using standard patterning techniques, the silicon dioxide anchor layer 78 is patterned such that it forms sidewalls 80 surrounding electrolyte cells 76 as well as contact window 82 through the top of silicon dioxide anchor 78 for access to electrolyte cell 76. Contact window 82 should be smaller than the top surface of electrolyte cell 76 so that a retaining rim 84 is formed around the cell perimeter. In a subsequent step, these contact windows 82 will be used to allow access to electrolyte cells 76. Contact windows 82 shoud be made as large as possible while still maintaining enough of a retaining rim 84 to secure cells 76.

Figure 6:
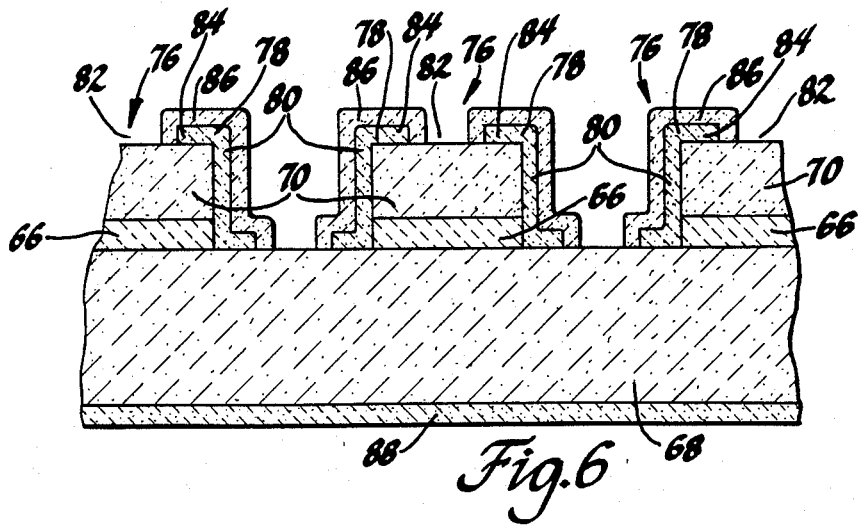
FIG. 6 is a cross-sectional view depicting the next step in forming the electrolyte cells in which a layer of silicon nitride is deposited on the electrolyte cell structures and patterned to form cell anchor covers.

To ensure that oxygen does not travel through the sides of electrolyte cells 76 and cell anchors 78, thus producing false sensor readings, silicon dioxide cell anchors 78 are covered with an oxygen impermeable layer 86 of silicon nitride as shown in FIG. 6. In a later-described alternate embodiment, the common metal electrode may be used for this purposes although that design is somewhat less desirable. However, if silicon nitride 86 is used to cover all anchors 78 it must be patterned such that it completely covers the anchors without sealing off contact windows 82 which may be accomplished by standard lithography and fluorine plasma etching. Both the silicon dioxide anchors 78 and silicon nitride anchor cover layer 86 must be patterned between the cell structures to allow access to the underlying silicon substrate 68 for the purpose of subsequently depositing electrode material. At operating temperatures of 300° to 800° C., it is quite possible that oxygen will in fact diffuse from the electrolyte cell through silicon dioxide anchors 78 and thus the use of silicon nitride as a barrier to oxygen diffusion is preferred. A layer 88 of silicon nitride is also deposited on the bottom of the silicon wafer 68 which serves to protect the bottom of the silicon wafer 68 which serves to protect the outer common electrode in a later processing step, as will become apparent.

Figure 7:
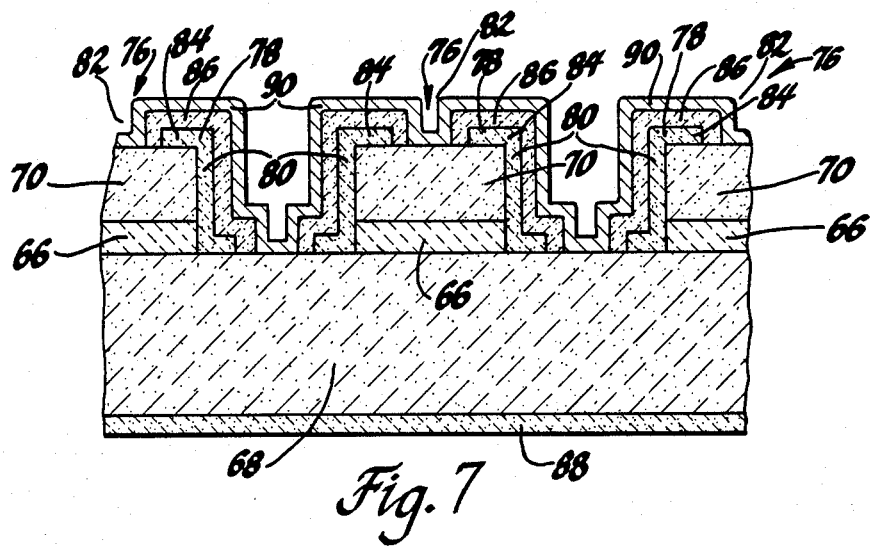
FIG. 7 is a cross-sectional view illustrating the next step in forming the electrolyte cells in which a common metal electrode is deposited on the electrolyte cells and the silicon body.

Referring now to FIG. 7, a porous internal common metal electrode 90 is deposited over the electrolyte cell structure 76 in ohmic contact with electrolyte layers 70 and overlying the silicon substrate 68. As previously mentioned, the silicon substrate 68 serves as the electrical connection between the internal and external common electrodes in the sensor. Common electrode 90 should be from about 0.1 micron to 1 micron thick although this dimension is not critical. Suitable electrode materials must be chemically stable throughout processing, must remain stable in an oxidizing ambient during operation, and must also have good mechanical stability and adhere well to silicon. They must, of course, also make ohmic contact to silicon and be suitably porous to allow for permeation of gas to the electrode-gas-electrolyte interface. A suitable ohmic contact provides a barrier to intermixing and diffusion of the electrode material and the silicon substrate. Silicides form such a stable barrier. Platinum has been found to be useful electrode material due to its excellent electrical conductivity and its ability to catalyze oxygen equilibration formation. Other electrode materials may be useful depending on the type of gas sensed and catalytic activity desired. By making the platinum electrodes porous, more area can be exposed for greater catalytic activity in the equilibration of exhaust gases in the case of an oxygen sensor.

In order to increase the adhesion of a platinum electrode 90 either directly to silicon dioxide anchors 78 in the absence of a silicon nitride cover layer, or to silicon nitride cover layer 86, a thin 0.1 micron layer (not shown) of polysilicon can be deposited and patterned over the silicon dioxide or silicon nitride prior to depositing the electrode 90. A platinum silicide layer may also be used for this purpose and, of course, both the polysilicon or platinum silicide layers would be patterned to conform to cell contact window 82 to allow contact by electrode 90 with the silicon substrate 68. Once electrode 90 has been deposited over the cell structures, the device is heated to form a platinum silicide where the electrode 90 contacts the silicon substrate 68.

In a later-discussed embodiment of the present invention having a three-cell configuration, the relatively large area electrolytes are further anchored by an overlying stiffening layer of silicon nitride or phosphosilicate glass in which channels are etched to expose the electrode-coated cell windows.

Figure 8:
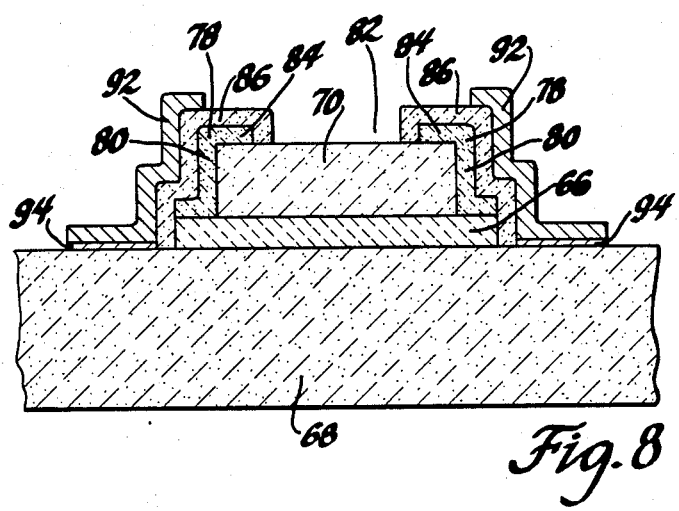
FIGS. 8, 9 and 10 are cross-sectional views depicting the sequential steps of an alternate process for forming the common metal electrode.
Figure 9:
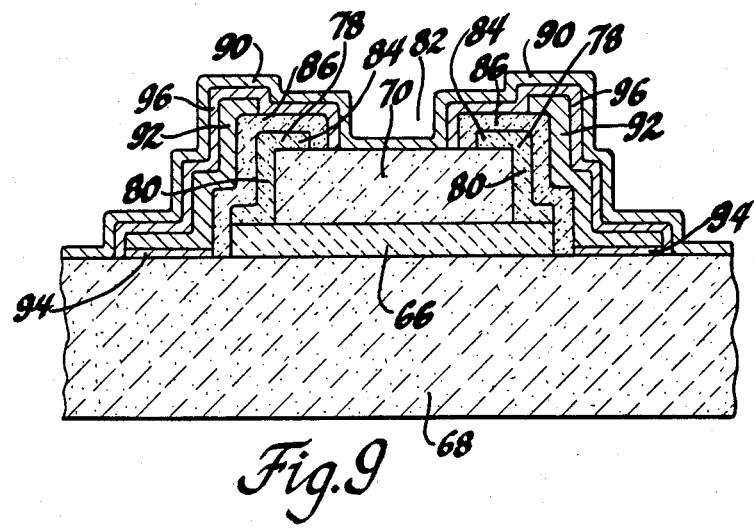

In another alternate embodiment, an electrode metallization scheme is provided which utilizes an independently deposited barrier metal that prevents intermixing and diffusion of silicon and platinum at the electrode-silicon interface. A suitable barrier metal has a positive free energy of reaction with silicon and platinum on its opposite faces and a large negative energy of formation. Certain transition metal carbides, borides, silicides, oxides and nitrides are suitable. We prefer to use titanium nitride due to its excellent thermodynamic stability, its high melting point and its inertness with noble metals such as platinum and gold. In this embodiment, as seen with reference to FIG. 8, titanium or a titanium-wolfram alloy 92 is deposited over the electrolyte cell in contact with the silicon substrate. The metal layer 92 is patterned such that it covers the majority of the underlying silicon nitride anchor cover layer 86 and, of course, it is in ohmic contact with the underlying silicon substrate 68. The silicon substrate 68 is then heated to between 700° to 900° C. for 15 to 30 minutes to form silicide 94 at the interface of the titanium-silicon, or titanium-wolfram-silicon interface. This layer then serves as a barrier region against intermixing of platinum and silicon. It has also been found that chromium is a suitable barrier metal for use herein. In order to protect the barrier metal from oxidation, it is preferred that a layer of gold 96 be deposited on the barrier metal and patterned such that it does not fill the electrolyte cell contact window as shown in FIG. 9. The barrier metal layer 92 and gold layer 96 are each only a few microns thick. Next, the internal common platinum electrode 90 is deposited on the cell in contact with the electrolyte.

Figure 10:
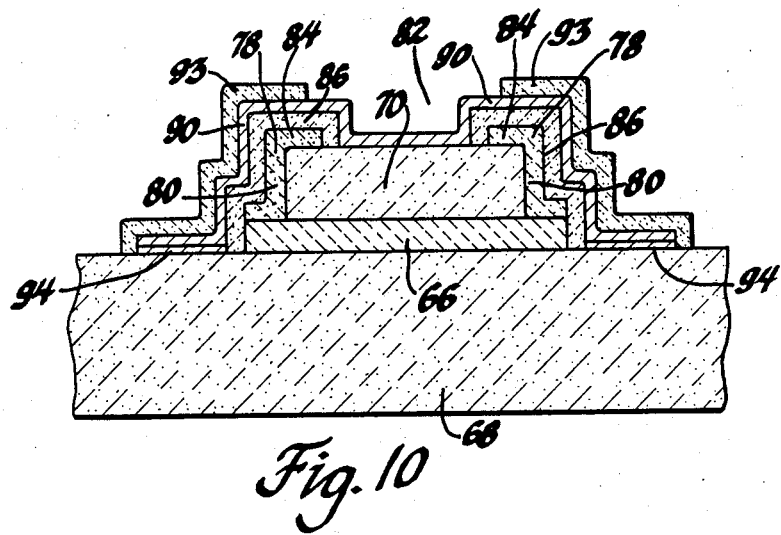

In still another embodiment, as shown in FIG. 10, the metallization scheme for forming the internal common electrode comprises depositing platinum electrode 90 over the cell in contact with the electrolyte 70 and silicon substrate 68 and then applying a layer of silicon nitride 93 over platinum electrode 90. The silicon nitride layer 93 is subsequently patterned using conventional photolithography and patterning techniques so that it does not cover the platinum electrode 90 at that portion which is in contact with electrolyte 70 through the cell window to allow the selected gas to enter and leave the sensor chamber. Again, a silicide 94 must be formed by heating the cell wafer. With any of the aforementioned alternative metallization schemes, the internal common electrode 90 is from 0.1 to 1 microns thick, preferably from 0.2 to 0.5 microns thick.

Figure 11:
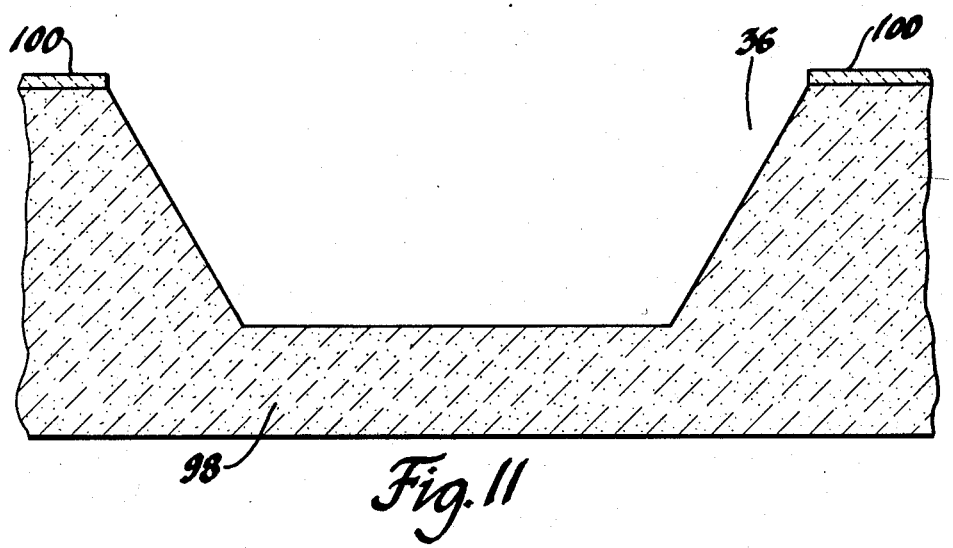
FIG. 11 is a cross-sectional view illustrating a preliminary step in a process for producing the cavity wafer which forms a part of the sensor of FIG. 1, wherein a cavity has been etched in a silicon wafer.

Referring now to FIG. 11, it is next necessary to prepare the top cover or cavity wafer 34 to be bonded to the previously described substrate wafer 68. A (100) oriented silicon wafer 98 is anisotropically etched to form cavity 36 which, when bonded to the substrate wafer 68, has an internal volume from about 1 to 20 nanoliters, preferably about 10 nanoliters. In forming the wafer cavity 36, wafer 98 is covered with a layer 100 of either silicon dioxide or silicon nitride which is shown patterned to form a mask having an opening of sufficient size to create cavity 36 of the preferred dimensions. Of course, it will be apparent to those skilled in the art that other materials may be used as a suitable mask during this step. Potassium hydroxide and ethylenediamine pyrocatechol are preferred etchants used in forming the cavity because they provide accurate (111) orientation sidewalls of the etched cavity and are self-limiting anisotropic etchants. Cavity 36 must be large enough so that the cavity walls do not come in contact with the sense and pump cells which it houses, yet be small enough to provide the requisite internal volume once bonded to substrate wafer 68 of between 1 and 20 nanoliters which yields an acceptable sensor response time.

Figure 12:
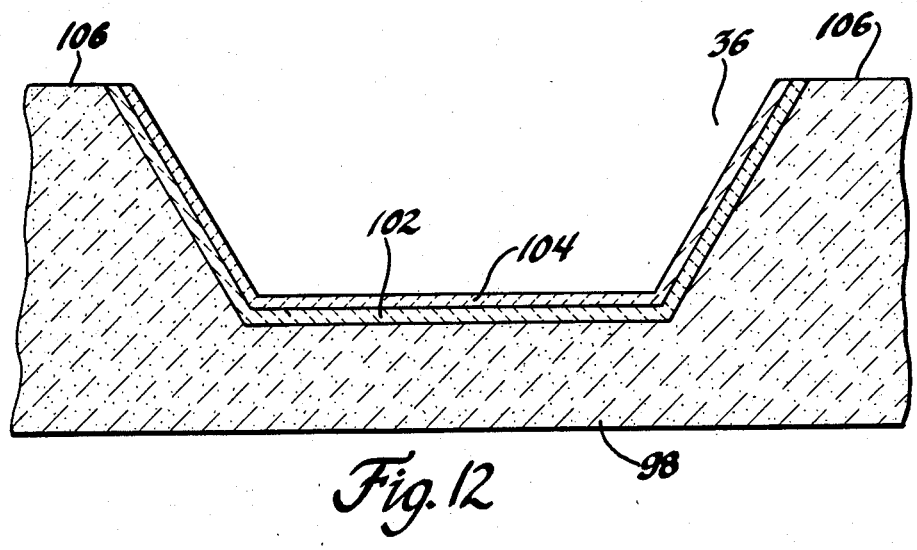
FIG. 12 is a cross-sectional view showing the next step in the process for forming the cavity wafer in which layers of silicon dioxide and silicon nitride are deposited in the wafer cavity.
Figure 13:
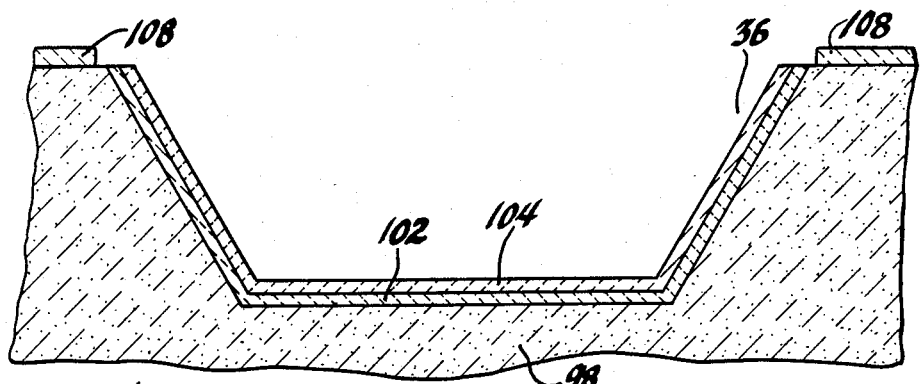
FIG. 13 is a view similar to FIG. 12 but showing the next step in the process in which a layer of germanium is deposited over the silicon nitride.
Figure 14:
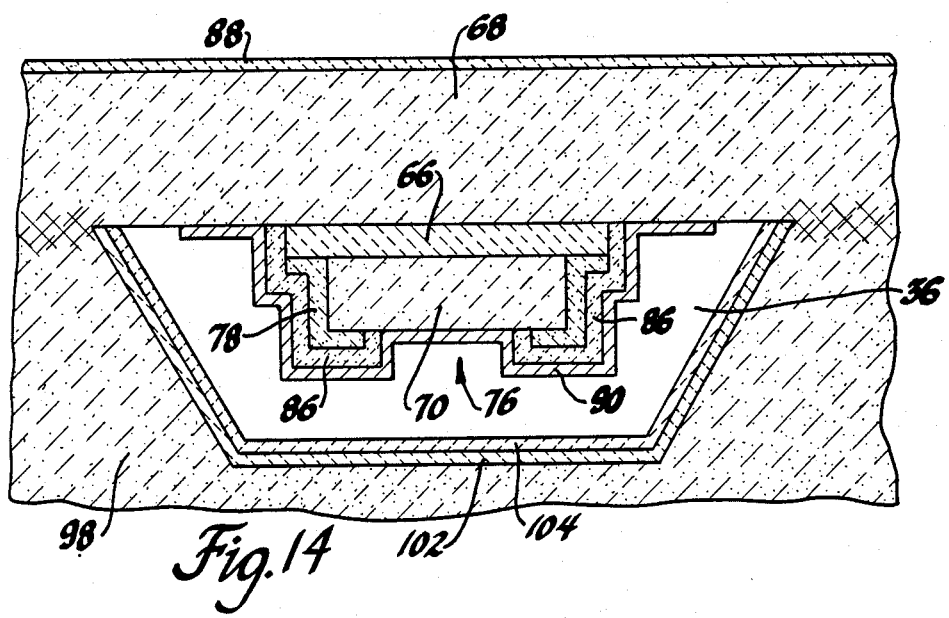
FIG. 14 is a cross-sectional view depicting the next step in the process for forming the sensor of FIG. 1 in which the cavity wafer is bonded to the electrolyte cells, only a single cell being shown.

As seen in FIG. 12, the mask 100 is then removed from etched cavity wafer 98 and a layer of silicon dioxide 102 and a layer of silicon nitride 104 are successively deposited over cavity wafer 98. Silicon dioxide layer 102 and silicon nitride layer 104 are removed from the lateral cavity wafer surfaces 106 which provides a clean surface for subsequent deposition of a bonding layer. Silicon dioxide layer 102 and silicon nitride layer 104 covering the internal etched cavity surfaces may not be necessary if the change in volume of the cavity due to oxidation during operation is not large. However, they are preferred for use in order to eliminate any cavity oxidation. Silicon dioxide layer 102 may be from about 0.07 to 0.1 microns thick and silicon nitride layer 104 may be from about 0.05 to about 0.1 microns.

Next, the substrate wafer 68 and cavity wafer 98 are bonded together to form a hermetically sealed chamber. Any technique which produces a strong hermetic bond is satisfactory. For example, cavity wafer 98 and substrate wafer 68 could be bonded together by solid-solid diffusion, anodic bonding, soldering or the like. As can be seen from FIG. 13, one may elect to use a bonding layer 108 to hermetically seal the substrate wafer 68 to cavity wafer 98.

Figure 15:
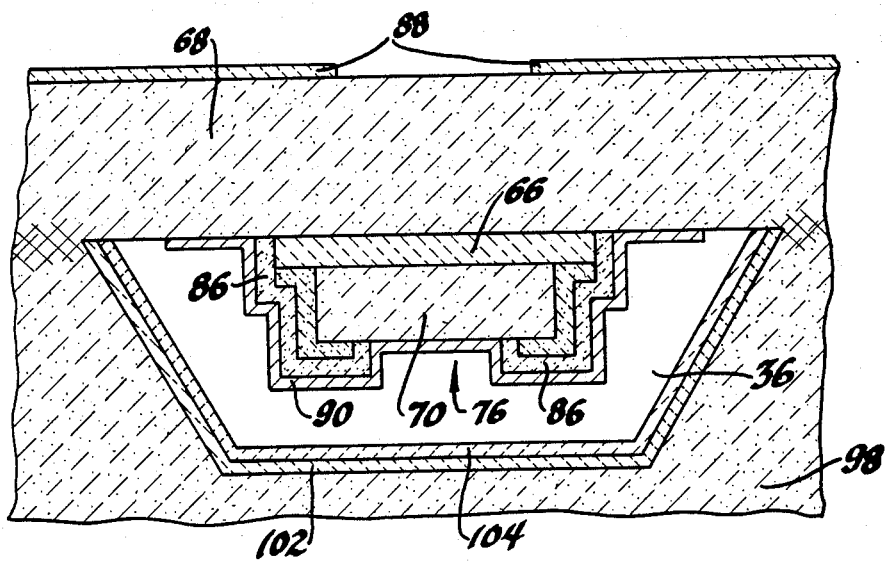
FIGS. 15-19 are cross-sectional views respectively depicting the successive steps for forming the outer electrodes of the electrolyte cells of the sensor shown in FIG. 1.
Figure 16:
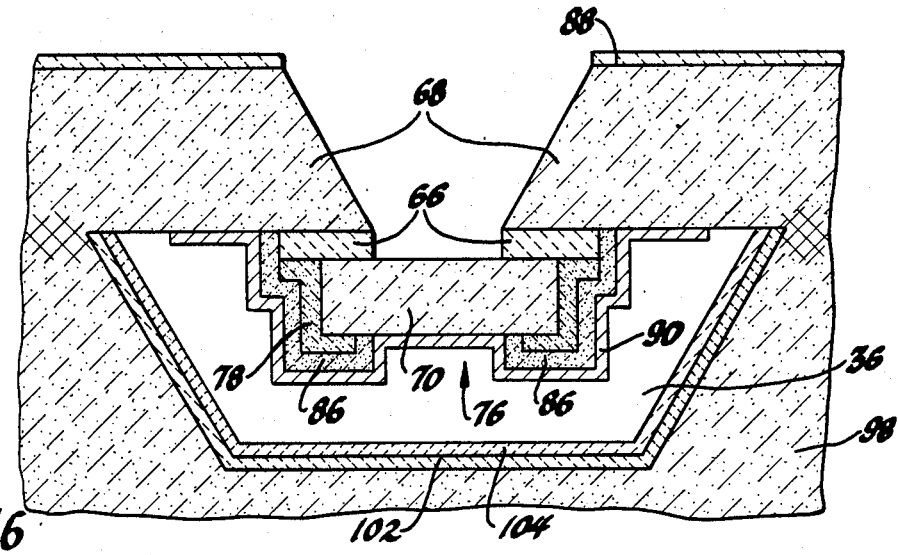
Figure 17:
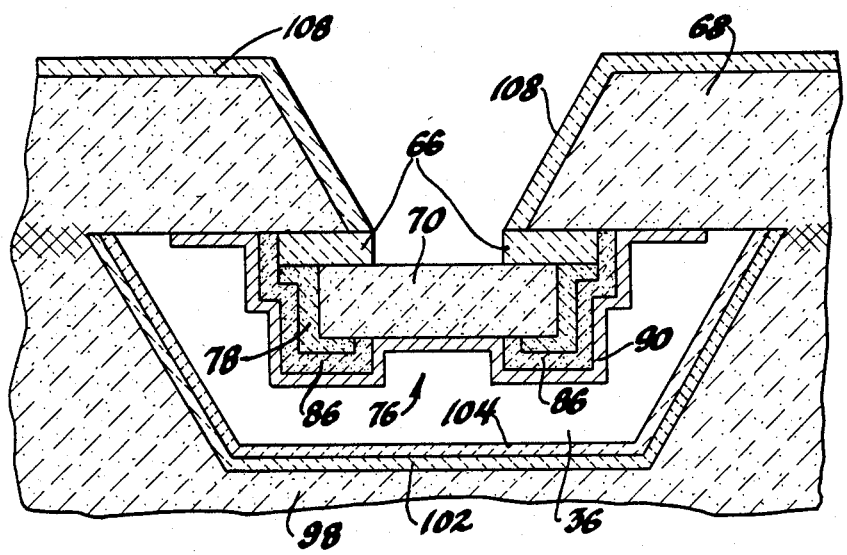

Next, an opening is created through the substrate wafer 68 and silicon dioxide layer 66 underlying the electrolyte cell 76 so that external electrodes can be deposited in contact with electrolyte layer 70. To accomplish this, a layer of silicon nitride 88 is deposited on the exterior surface of silicon wafer 68 and is patterned as shown in FIG. 15 to form a mask window through which the external electrode contact window is to be etched. Using standard photolithography and patterning techniques, the silicon wafer 68 is then anisotropically etched. Typical anisotropic etching techniques will be self-limiting, creating (111) orientation sidewalls in the silicon cell wafer 68. Furthermore, once the etchant reaches the underlying silicon dioxide layer 66, it will cease etching. After the silicon wafer 68 has been etched, silicon nitride mask 88 is removed while simultaneously etching away that portion of the silicon dioxide layer 66 which remains between the contact window and the electrolyte layer 70 as shown in FIG. 16. At this point, the electrolyte layer 70 can be readily accessed through the contact window.

Figure 18:
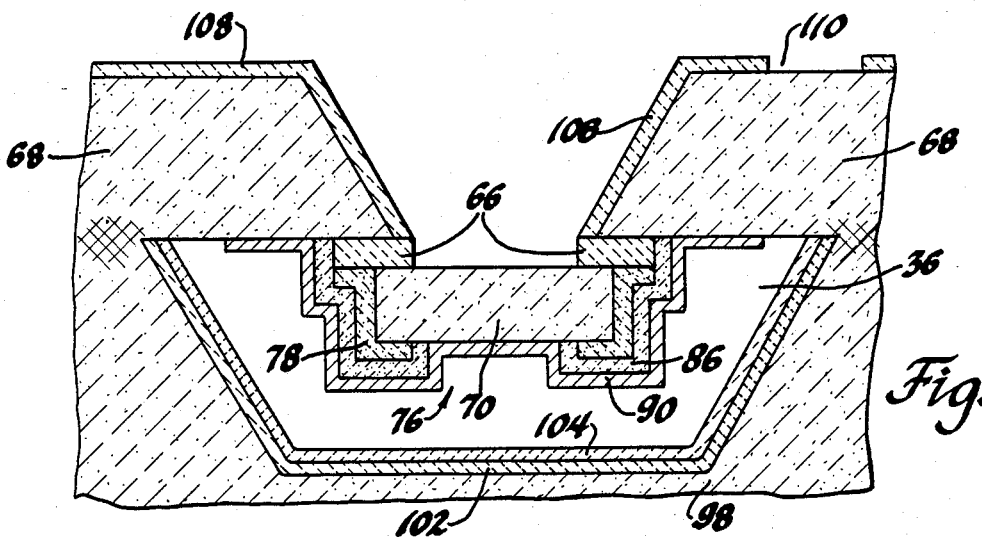

In order to insulate the silicon wafer 68 from the exterior pump and sense electrodes which are electrodes 48 and 50 in FIG. 1, the wafer 68 is oxidized to form silicon dioxide layer 109 approximately 0.2 to 0.5 microns thick. Since this oxide layer 109 must isolate the pump and sense electrodes 48 and 50 from the substrate wafer 68, it must completely cover the sidewalls of the window. Since the silicon substrate 68 forms an electrical contact with the internal electrode 90, a portion 110 of silicon dioxide layer 109 must be removed as illustrated in FIG. 18 to allow an external common electrode to be deposited in electrical contact with the silicon substrate.

Figure 19:
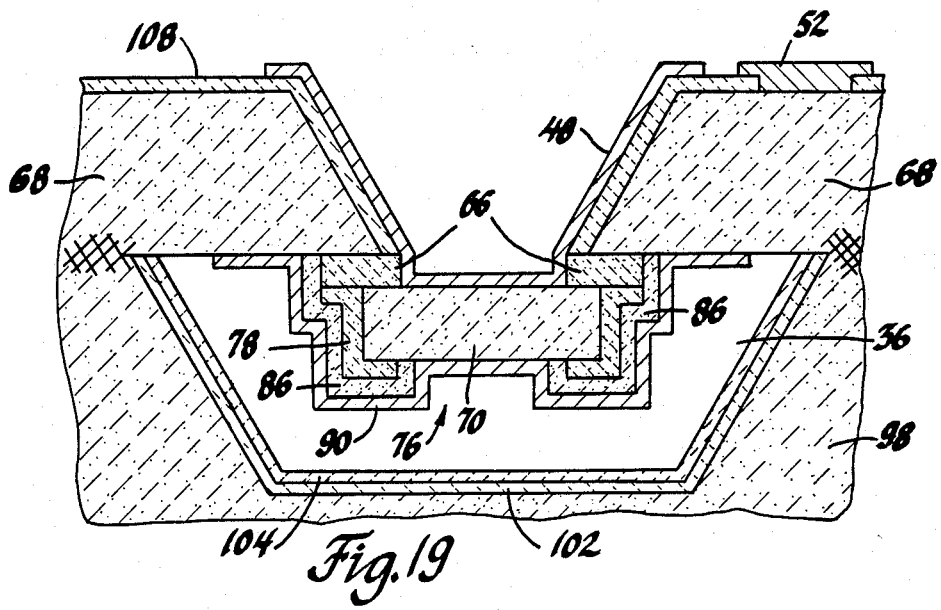

Finally, as depicted in FIG. 19, porous external pump and sense electrodes 48 and 50 (only one shown) and external common electrode 52 are deposited by sputtering platinum or other suitable electrode materials as previously discussed onto oxide-coated wafer 68 and, utilizing standard lithography and etching techniques, the electrodes 48, 50, 52 are patterned appropriately. It may be necessary to selectively precoat the sidewalls of silicon dioxide layer 108 with titanium or titanium nitride to assure good adherence of platinum to the underlying surface.

Figure 20:
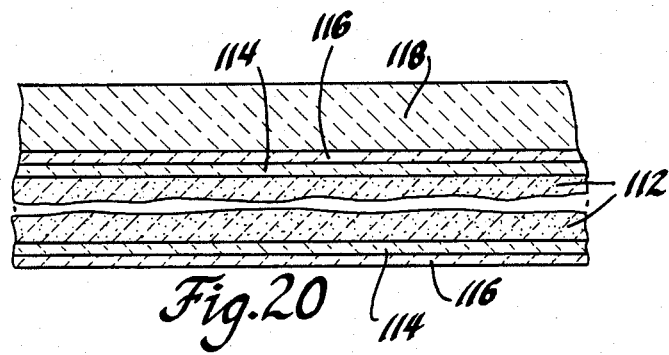
FIG. 20 is an enlarged, fragmentary cross-sectional view of an alternate form of a multi-layer substrate upon which the electrolyte cells can be formed.
Figure 21:
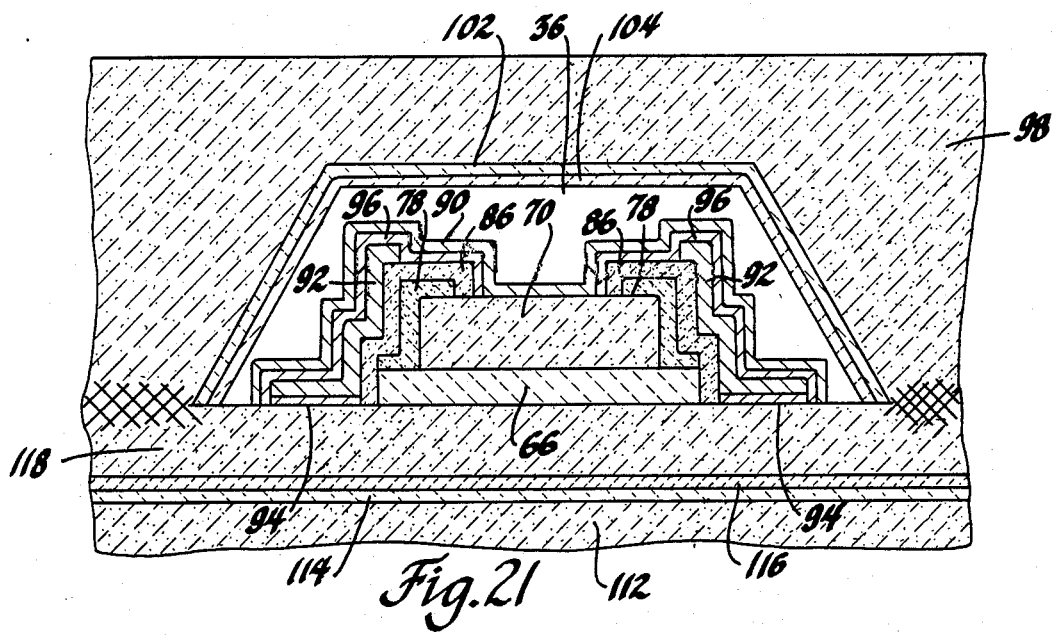
FIG. 21 is a cross-sectional view of a single sensor cell employing the substrate shown in FIG. 20.
Figure 22:
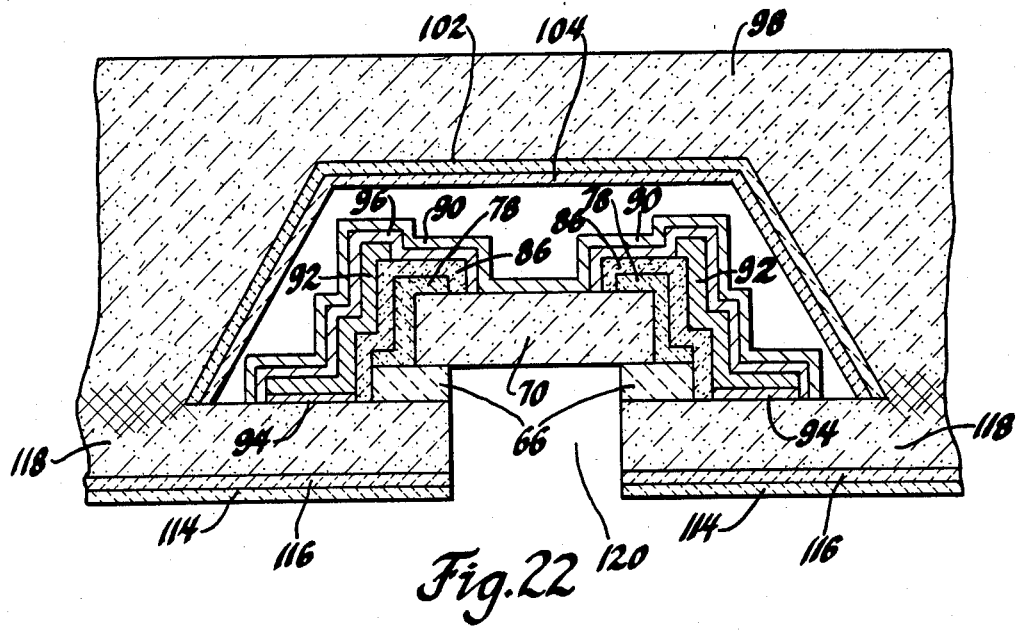
FIG. 22 is a view similar to FIG. 21, but wherein a contact window and an external electrode have been formed, the silicon dioxide layer underlying the electrolyte cell having been removed.

In an alternative embodiment, windows for the external electrodes 48, 50 are more efficiently formed by using a doped polysilicon cell wafer body or substrate instead of a silicon cell wafer body. Referring now to FIG. 20, silicon wafer 112 is oxidized to form silicon dioxide layer 114 which should be approximately 0.1 to 0.3 microns thick. A silicon nitride layer 116 approximately 0.1 to 0.3 microns thick is then deposited on silicon dioxide layer 114. A doped polysilicon layer 118, approximately 5 to 10 microns thick, is deposited on silicon nitride layer 116. The electrolyte cells and anchoring structures are then formed on polysilicon layer 118 in the same manner as formed on a silicon substrate as previously described. The cavity wafer is also formed in the manner previously described and the cavity wafer and substrate wafer are then bonded together as shown in FIG. 21. Referring now to FIG. 21, silicon wafer 112 is etched off selectively using an etchant, while protecting the rest of the assembly with an etch-resistant coating. An etchant bath is chosen which is self-limiting. That is, after silicon wafer 112 is etched completely away, the etching process stops at silicon dioxide layer 114. Silicon dioxide layer 114 and silicon nitride layer 116 are then patterned to form a window 120 to the electrolyte cell body 70. Silicon dioxide layer 114, silicon nitride layer 116 and polysilicon layer 118 can then be etched in sequence using standard techniques. Since polysilicon layer 118 is relatively thin, i.e. 5 to 10 microns, and because polysilicon can be etched isotropically, the window opening 120 to the electrolyte cell may be much smaller than when the electrolyte cell is formed on a silicon substrate.

Figure 23:
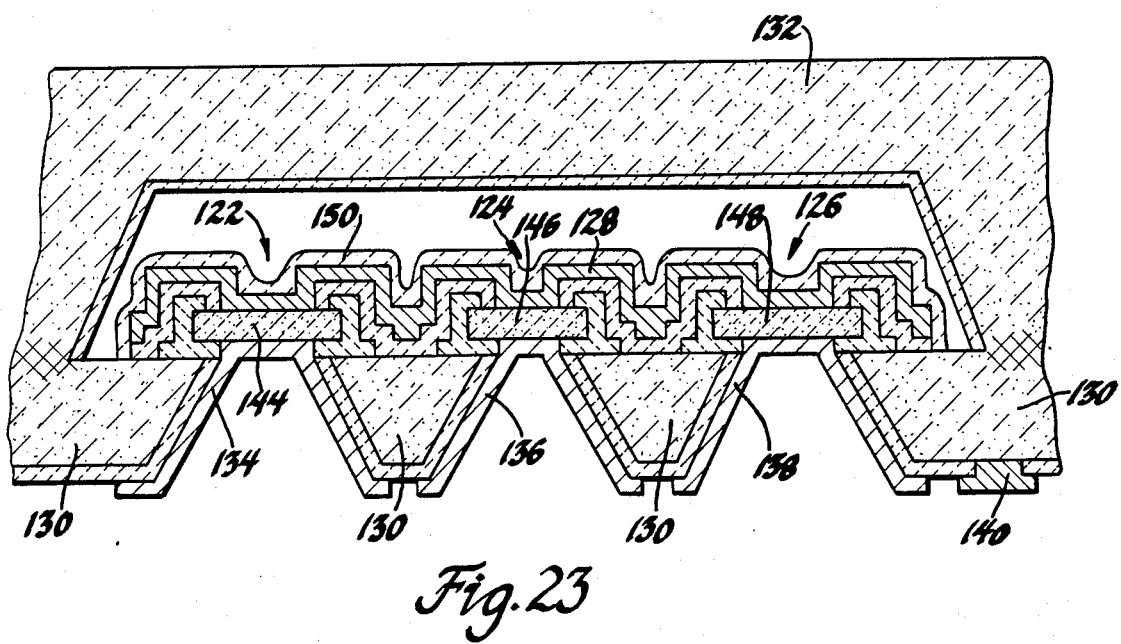
FIG. 23 is a fragmentary cross-sectional view of an alternate form of the gas sensor of the present invention which employs a sense cell and a pair of pump cells.

An alternate embodiment of the oxygen sensor is depicted in FIG. 23 which is similar to that described above with reference to FIG. 1, but employs a pair of pump cells 122, 126 and a single sense cell 124 interconnected by a common internal electrode 128. The cells 122, 126 are adapted to be connected with external circuitry by means of external electrodes 134, 138 and a common electrode 140. The cells 122,126 are formed on a semiconductor substrate 130 and are covered by a cavity wafer 132 similar to that previously described. Because the electrolyte films 144, 148 of the cells 122, 126 are relatively large in area, they are subject to greater flexing in response to gas pressure differentials. In order to reduce such flexing, a stiffening layer 150 of $Si_3N_4$ or phosphosilicate glass is deposited over the upper surface of the cells 122,126. The stiffening layer 150 provides rigidity and additional weight on the electrolyte layers 144, 148, thereby controlling their flexing.

Figure 24:
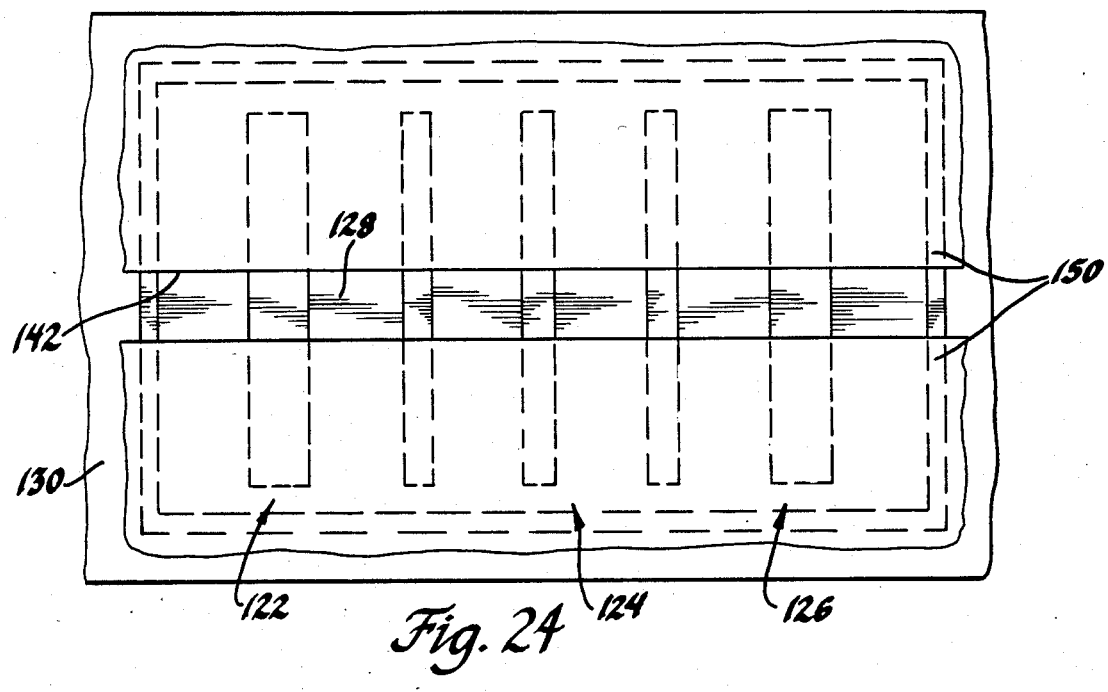
FIG. 24 is a plan view of the gas sensor shown in FIG. 23, the cavity wafer having been removed, wherein the broken line indicates the position of a channel to be formed in the stiffening layer.

FIG. 24 is a plan view of the gas sensor shown in FIG. 23, the covering cavity wafer 132 having been removed. In order to expose those portions of the common interior electrode 128 which overlie the electrolytic layers 144, 148 to gas within the sensor, a series of channels, one being indicated at 142, are formed in the stiffening layer 150. The channels 142 extend transversely to the longitudinal dimension of the cells 122, 126, and as many of the channels 142 are provided as is required to obtain the necessary area of exposure of the interior common electrode 128.

Figure 25:
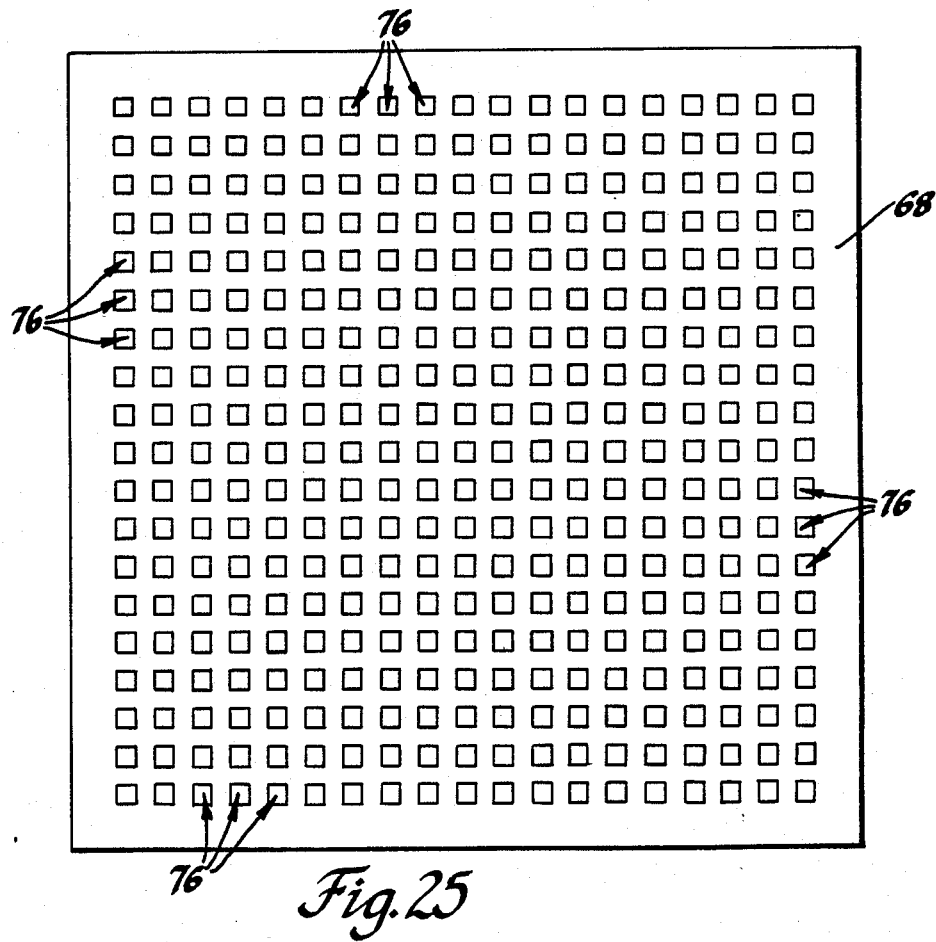
FIG. 25 is a plan view of a substrate having an array of pump and sense cells formed thereon.

As previously indicated, in order to minimize the amount of flexing of the electrolytic layers of the pump and sense cells, such cells may be formed in an array thereof, as diagrammatically illustrated in FIG. 25. Each of the cells 76 is of relatively small dimensions, typically, for example, 110×110 microns, in contrast to the relatively large area displaced by the cells of the gas sensor shown in FIG. 1 or FIG. 23. The individual cells 76 may be electrically interconnected (not shown) using well known microelectronics processing technology, yet are spaced far enough apart to reduce the amount of flexing of the substrate 68, and therefore the electrolytic layer of each cell 76.

From the foregoing, it is apparent that the gas sensor and method of making same described above not only provide for the reliable accomplishment of the objects of the invention but do so in a particularly economical and effective manner. It is recognized, however, that those skilled in the art may make various modifications or additions to the preferred embodiment chosen to illustrate the invention without departing from the spirit and scope of the present contribution to the art. One example of this is that the cavity 36 could be provided in substrate wafer 32 instead of wafer 34, of FIG. 1. In such instance, cells 38 and 40 would be formed on the bottom of a recess in substrate wafer 32, and wafer 34 could simply be a flat plate. Accordingly, it is to be understood that the protection sought and to be afforded hereby should be deemed to extend to the subject matter claimed and all equivalents thereof fairly within the scope of the invention.

What is claimed is:

1. A gas sensor for measuring the amount of a selected gas in a gaseous environment, comprising:
    a sensor body adapted to have a portion exposed to said gaseous environment, said sensor body including an essentially planar substrate having a closed chamber for containing a quantity of said selected gas;
    first means in said chamber having access to a source of said selected gas for electrochemically pumping a predetermined quantity of said selected gas into and out of said chamber; and
    second means in said chamber, having access to said selected gas in said chamber and to said gaseous environment outside said chamber, for sensing the concentration of said selected gas in said environment relative to the predetermined quantity of said selected gas in said chamber,
    said first and second means being disposed on said substrate and within said chamber.

2. The gas sensor of claim 1, wherein said first and second means respectively include first and second electrolyte cells for conducting ions of said selected gas and at least a portion of said substrate is electrically conductive, said sensor further including:
    a first conductor electrically connecting said first and second cells with said conductive portion of said substrate, said first conductor being defined by a layer of electrically conductive material deposited on one side of said substrate, and
    a second conductor adapted to electrically connect said conductive portion of said substrate with an external circuit, said second conductor being defined by a layer of electrically conductive material deposited on the opposite side of said substrate.

3. The gas sensor of claim 1, wherein:
    said first and second means respectively include first and second electrolyte cells formed on one side of said substrate for conducting ions of said selected gas,
    said substrate includes a pair of windows therethrough respectively registered with said first and second cells, and
    said sensor further includes a pair of electrical conductors respectively adapted to connect said first and second cells with an external circuit, said pair of conductors being respectively defined by layers of an electrically conductive material deposited on the other side of said substrate and extending through said windows and contacting the corresponding cells.

4. The gas sensor of claim 3 wherein each of said windows is defined by sidewalls and the corresponding layer of conductive material includes a portion overlying at least a part of said sidewalls and contacting the associated cell, said sidewalls being spaced apart to allow the selected gas to pass through said window.

5. The gas sensor of claim 3 wherein a portion of said substrate between said windows is electrically conductive and is electrically insulated from said pair of conductors, said sensor including a third conductor electrically connecting said cells with said conductive portion of said substrate and defined by a layer of electrically conductive material deposited on said one side of said substrate, and a fourth electrical conductor forming an external electrical contact on said sensor body and defined by a layer of electrically conductive material deposited on the other side of said substrate and contacting said electrically conductive portion thereof.

6. The gas sensor of claim 5, wherein said electrically conductive portion of said substrate is defined by a semiconductor material.

7. The gas sensor of claim 1, wherein said first and second means each includes a layer of electrolytic material on said substrate for conducting ions therethrough and means for anchoring said layer of electrolytic material to said substrate, said anchoring means including a layer of insulative material deposited on said substrate and overlying portions of said layer of electrolytic material.

8. The gas sensor of claim 7, wherein said first and second means each includes a layer of barrieer material surrounding the corresponding layer of electrolytic material and preventing the diffusion of ions of said selected gas therethrough.

9. The gas sensor of claim 8, wherein said layer of barrier material is silicon nitride.

10. The gas sensor of claim 7, wherein each of said layers of electrolytic materials is zirconium dioxide.

11. The gas sensor of claim 7, wherein said layer of insulative matrerial is silicon dioxide.

12. The gas sensor of claim 1, wherein:
said substrate is defined by a semiconductor material and includes at least a pair of windows therethrough through which said selected gas may pass, and
said first and second means includes an electrolyte cell for conducting ions of said selected gas therethrough, said cells being respectively defined by layers of an electrolytic material on one side of said substrate and respectively overlying said windows,
said sensor further including a first layer of electrically conductive material on said one side of said substrate and electrically connecting at least a portion of said substrate with one side of each of layers of said electrolyte material, second and third layers of an electrically conductive material respectively overlying the opposite sides of said layers of electrolytic material and extending across the corresponding window whereby to form an interface between the volume of space within the window and the opposite side of the layer of electrolytic material, and a fourth layer of electrically conductive material on the opposite side of said substrate and defining an external electrical contact on said sensor body, said external contact being electrically connected with said one side of said layers of electrolytic material through said substrate and said first layer of conductive material.

13. The gas sensor of claim 12, wherein portions of said second and third layers of electrically conductive material cover at least a portion of the sidewalls of said substrate which define said windows and a portion of the opposite side of said substrate to define external electrical contacts on said sensor body, said sensor including means for electrically insulating said portions of said second and third layers of electrically conductive material from said substrate.

14. The gas sensor of claim 12, wherein said electrolytic material is zirconium dioxide.

15. The gas sensor of claim 12, wherein said electrically conductive material defining said first, second and third layers thereof is relatively porous platinum.

16. The gas sensor of claim 12, wherein said second and third layers of electrically conductive material are defined by a relatively porous metal having a thickness no greater than approximately 500 nanometers.

17. The gas sensor of claim 1, wherein said sensor body includes a cover hermetically sealed to said substrate.

18. The gas sensor of claim 17, wherein said cover is defined by an oxidizable material and has the interior surface thereof covered with a layer of non-oxidizable material.

19. The gas sensor of claim 1, wherein said chamber possesses a volume of no greater than approximately 20 nanoliters.

20. The gas sensor of claim 1, wherein said sensor body includes two semiconductor wafers bonded together to form said closed cavity, one of said wafers defining said substrate.

21. The gas sensor of claim 1, wherein said substrate includes a layer of doped polysilicon.

22. A gas sensor for measuring the concentration of a gaseous component in a gaseous environment, comprising:
a sensor body adapted to be introduced into said gaseous environment and including a closed chamber for containing a quantity of said gaseous component therein, said sensor body including a substrate defining at lease a portion of said chamber, said substrate including first and secnd openings therethrough;
a pump cell on said sensor body for pumping said gaseous component between said chamber and said gaseous environment, said pump cell including a first layer of solid material exhibiting ion conduction, said first layer being disposed within said chamber on one side of said substrate and covering said first opening in said substrate;
a sensing cell on said sensor body for sensing the concentration of said gaseous component contained within said chamber, the concentration of said gaseous component contained in said chamber being related to the amount of the gaseous component in said gaseous environment, said sensing cell including a second layer of solid material exhibiting ion conduction, said second layer being disposed within said chamber on said one side of said substrate and covering said second opening in said substrate; and
first and second electrodes respectively forming ohmic contacts on one side of said first and second layers of solid material and respectively extending across said first and second openings in said substrate.

23. The gas sensor of claim 22, wherein a portion of said substrate is electrically conductive and said gas sensor further includes a first layer of electrically conductive material electrically connecting one side of said conductive portion of said substrate with the other side of the first and second layers of solid material, and a second layer of electrically conductive material on the other side of said conductive material defining an external electrical contact on said sensor body.

24. The gas sensor of claim 22, wherein each of said cells includes a deposited layer of insulative material covering portions of the corresponding layers of solid materials and said substrate for anchoring said layers of solid materials to said substrate.

25. The gas sensor of claim 22, wherein said first and second electrodes are respectively defined by layers of deposited electrically conductive material on the opposite side of said substrate, said layers of conductive material providing a pair external electrical contacts on said sensor body.

26. The gas sensor of claim 22, wherein said gas sensor includes a plurality of the pump cells and the sensing cells arranged in an array on said substrate and disposed within said chamber.

27. The gas sensor of claim 22, wherein:
said substrate comprises a semiconductor material, and
said sensor body further includes a cover of semiconductor material hermetically bonded to said substrate.

28. The gas sensor of claim 27, wherein said cover includes a cavity therein which partially defines said chamber, the walls of said cover defining said cavity including a layer of non-oxidizable material thereon.

29. A gas sensor for determining the concentration of a selected gas in a gaseous environment, comprising:
a sensor body including first and second portions of semiconductor material and defining a hermetically sealed chamber therebetween within which a quantity of said selected gas may be contained, said first and second portions being joined together by covalent bonding defining a homogenous interface between said first and second portions;
first means on said sensor body for pumping said selected gas into and out of said chamber; and
second means on said sensor body for sensing the concentration of gas contained in said chamber relative to the concentration of said selected gas in said environment, the concentration of gas contained in said chamber being related to the concentration of said selected gas in said gaseous environment.

30. The gas sensor of claim 29, wherein said first portion of said sensor body is defined by a planar substrate and said second portion is defined by a cover having a cavity therein, and wherein said cavity partially defines said chamber.

31. The gas sensor of claim 30, wherein the walls of said cover defining said cavity are covered by a layer of non-oxidizable material.

32. The gas sensor of claim 30, wherein said semiconductor material is silicon.

33. The gas sensor of claim 30, wherein the peripheral edges of said first and second portions are joined together by said covalent bonding.

34. The gas sensor of claim 29, wherein said chamber has a volume of no greater than approximately 20 nanoliters.

35. A method of making a gas sensor for determining the concentration of a selected gas in a gaseous environment, said sensor being of the type including a sensor body provided with a chamber within which a quantity of said selected gas may be contained, a pump cell for pumping said selected gas into and out of said chamber, and a sensing cell for sensing the concentration of said selected gas in said chamber relative to the concentration of the selected gas in said gaseous environment, said method comprising the steps of:
(a) forming said pump cell and said sensing cell on a first substrate;
(b) forming a cavity in a second substrate;
(c) joining said first and second substrate together to form said chamber.

36. The method of claim 35, wherein step (a) includes the steps of:
depositing a layer of material on one side of said substrate which exhibits ion conduction;
removing portions of the deposited ion conducting layer to define spaced apart discrete sections of said ion conducting material, said discrete sections of said ion conducting material respectively forming portions of said pump cell and said sensing cell.

37. The method of claim 36, wherein step (a) includes the steps of:
forming a pair of windows in said substrate which respectively register with and expose portions of said discrete sections of said ion conducting material,
forming a pair of electrodes respectively on said exposed portions of said discrete sections of said ion conducting material.

38. The method of claim 37, wherein said electrodes are formed by vapor depositing a layer of conductive material on the opposite side of said substrate and into said windows, and then etching away portions of said layer of conductive material.

39. The method of claim 36, wherein step (b) is performed by applying a mask on said second substrate which exposes at least a portion of said second substrate and then etching away said exposed portion of said second substrate.

40. The method of claim 39, including the step of forming a layer of non-oxidizable material on said second substrate and within said cavity to prevent the oxidation of the walls of said cavity.

41. The method of claim 36, wherein said first and second substrates include a silicon material and step (c) is performed by:
depositing a layer of material on one of said substrates which is miscible in silicon,
placing the substrates in face-to-face contact with the layer of miscible material pressed therebetween,
pressing said substrates together to apply pressure at the area of contact therebetween, and
heating said area of contact to a temperature sufficient to melt said miscible layer whereby the interface between said substrates at said contact area is substantially homogeneous.

42. The method of claim 35, wherein step (a) includes the steps of:
depositing a layer of material on said one side of said substrate which covers said discrete sections of said ion conducting material and which forms a gas impenetrable barrier around said discrete sections, forming windows in said barrier forming layer which respectively expose portions of said discrete sections, and forming an electrode on each of said exposed portions of said discrete sections.

43. The method of claim 42, wherein:

said windows are formed by etching said barrier forming layer, and said electrodes are formed by depositing a layer of said conductive material on said one side of said substrate and then etching away undesired portions of said deposited layer of conductive material.

44. A method of making a gas sensor for determining the concentration of a selected gas in a gaseous environment and of the type which includes a sensor body, a chamber within which a quantity of the selected gas may be contained, a pump cell for pumping said selected gas into and out of said chamber, and a sensing cell for sensing the concentration of said selected gas in said chamber relative to the concentration of the selected gas in said gaseous environment, said method comprising the steps of:

(a) depositing a plurality of layers of material on a substrate; and (b) selectively etching away undesired portions of said vapor deposited layers to define said pump cell and said sensing cell.

45. The method of claim 44, wherein step (a) includes the steps of depositing a layer of material on one side of said substrate which exhibits ion conduction, and step (b) includes the step of etching away undesired portions of said ion conducting layer to define two discrete sections of said ion conducting layer which respectively form portions of said pump cell and said sense cell.

46. The method of claim 45, wherein step (a) includes the step of depositing a layer of electrically insulative material on said substrate before the layer of ion conducting material is deposited and step (b) includes the step of etching away a portion of the insulative layer between the discrete sections of said ion conducting layer.

47. The method of claim 45, wherein step (a) includes the step of anchoring the discrete sections of said ion conducting layer to said substrate by depositing a layer of anchoring material over said discrete sections of said ion conducting layer and onto said substrate and forming contact windows in only a portion of the layer of anchoring material which covers said discrete sections.

48. The method of claim 45, wherein step (a) includes the step of forming a gas impenetrable barrier around said discrete sections of said ion conducting layer by depositing a layer of gas impenetrable material over said discrete sections and then removing portions of said gas impenetrable layer.

49. The method of claim 45, including the step of electrically connecting said discrete sections of said ion conducting layer by vapor depositing a layer of conductive metal on said substrate and overlying said discrete sections and then selectively removing portions of said conductive layer to define an electrical connection between said discrete portions.

50. The method of claim 45, including the steps of:

forming a pair of windows through said substrate which respectively expose one side of said discrete sections of said ion conducting layer, and forming a pair of electrodes on said exposed portion of said discrete sections.

51. The method of claim 50, wherein said windows are formed by etching through said substrate and said electrodes are formed by vapor depositing a layer of conductive metal on the opposite side of said substrate and selectively etching away undesired portions of said conductive metal layer.

52. The method of claim 44, including the step of etching a cavity in a semiconductor wafer and then bonding said wafer to said substrate.

53. The method of claim 52, wherein said substrate and said wafer are silicon and said bonding step is performed by introducing a layer of material between said substrate and said wafer which is miscible in silicon and heating said miscible material to form a covalently bonded, homogeneous, hermetically sealed interface between said wafer and said substrate.

* * * * *